United States Patent [19]

Alburn et al.

[11] 4,061,737

[45] Dec. 6, 1977

[54] METHOD FOR STIMULATING RELEASE OF PROLACTIN

[75] Inventors: Harvey E. Alburn, West Chester; Eric L. Lien, Paoli; Norman H. Grant, Wynnewood, all of Pa.

[73] Assignee: American Home Products Corporation, New York, N.Y.

[21] Appl. No.: 754,795

[22] Filed: Dec. 27, 1976

[51] Int. Cl.² .............................................. A61K 37/00
[52] U.S. Cl. ..................................................... 424/177
[58] Field of Search ......................................... 424/177

[56] References Cited
PUBLICATIONS

Lien, et al., Life Science 19, pp. 837–840, 1976.
M. Brown, et al., Endocrinology 97, 1151–1156 (1975).
C. Rivier, et al., Endocrinology 100, 238–241 (1977).
J. Hughes, et al., Nature 258, 577–579 (1975).
C. Pert, et al., Science 194, 330–332 (1976).
E. Wei, et al., Chem. Abst. 85, 1976, p. 154355m.
A. Schally, Chem. Abst. 77, 1972, p. 29229g.
L. Lazarus, et al., Chem. Abst. 85, 1976, p. 104290r.
K. Medzihradszky, et al., Chem. Abst. 85, 1976, p. 137660q.
B. A. Morgan, et al., Chem. Abst. 85, 1976, p. 186907.

Primary Examiner—Delbert R. Phillips
Attorney, Agent, or Firm—David E. Frankhouser

[57] ABSTRACT

Prolactin release is stimulated by parenteral administration of a pentapeptide of the formula:

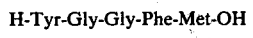

or

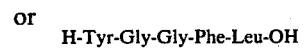

or a non-toxic pharmacologically acceptable acid addition salt thereof.

3 Claims, No Drawings

METHOD FOR STIMULATING RELEASE OF PROLACTIN

The hormones secreted by the pituitary gland control various body processes such as metabolism, growth, reproduction, and behavior. The secretion of the pituitary hormones is regulated by hormones from the hypothalamus which either stimulate or inhibit the release of the pituitary hormones. For example, growth hormone (somatotropin or GH) release is inhibited by the somatotropin release inhibiting factor (somatostatin or SRIF); luteinizing hormone (LH) release is promoted by the luteinizing hormone releasing factor (or LRF); and thyrotropin hormone and prolactin hormone release are both promoted by the thryotropin releasing factor (thyroliberin or TRH).

An important pituitary hormone is prolactin whose physiological functions include the promotion of mammary gland development and the induction of milk production. The present invention relates to a method for stimulating the release of prolactin.

In accordance with the present invention there is provided a method for stimulating prolactin release in a warmblooded animal in which such stimulation is desirable which comprises administering to said animal by a parenteral route an effective amount of a pentapeptide of the formula:

H-Tyr-Gly-Gly-Phe-Met-OH           I or

H-Tyr-Gly-Gly-Phe-Leu-OH           II or a non-toxic, pharmacologically acceptable salt thereof.

The pentapeptides represented by Formula I and II above are also known as "methionine-enkephalin" and "leucine-enkephalin", respectively. The pentatpeptides of Formula I and II are the components of "enkephalin", a substance isolated from pig brains which acts as an agonist at opiate receptor sites [see J. Hughes et al., Nature, 258, 577 (1975)]. Both peptides have been demonstrated to inhibit contractions of mouse vas deferens and guinea pig ileum and to inhibit stereospecific binding of $^3$H-naloxone to guinea pig brain, which activities are also elicited by morphine. It is known that morphine can raise prolactin levels [see G. Tolis et al., J. Clin. Endocrinol. Metab., 41, 797 (1975)].

The amino acid sequence of methionine-enkephalin is identical to that of the N-terminal portion of the C-fragment ($\beta$-endorphin or $\beta$-LPH[61-91]) of the peptide $\beta$-lipotropin, which is found in large concentrations in the pituitary. Both $\beta$-lipotropin and the C-fragment show morphine-like properties in various test systems.

In carrying out the method of the present invention, the pentapeptide I or II, or a mixture thereof, is dissolved in a physiologically acceptable aqueous medium, such as saline, and the solution is administered parenterally, i.e. by the subcutaneous (s.c.), intramuscular (i.m.) or intravenous (i.v.) route. A dose of from about 0.1 mg/kg. to about 10 mg/kg. of the peptide is effective in stimulating prolactin release.

Methionine-enkephalin, and leucine-enkephalin are synthesized by the solid phase method of Stewart and Young, Solid Phase Peptide Synthesis, W. H. Freeman, San Francisco, California (1969).

The ability of methionine- and leucine-enkephalin to stimulate prolactin release has been demonstrated in rats by intravenous and subcutaneous routes as described in the following examples:

EXAMPLE I

Male Charles River CD rats were injected with the enkephalin (in saline) or saline alone either subcutaneously or intravenously via the femoral vein. Fifteen minutes later the animals were decapitated and blood collected (12 mg. versene and 6000 units of Trasylol added per tube). Each plasma sample was assayed for prolactin in quadruplicate by specific double antibody radioimmunoassays, using NIAMDD reagents and the procedure of Neill and Reichert, Endocrinology, 88, 548 (1971).

The results of the testing are shown in Table I:

TABLE I

| Experiment | Prolactin Plasma Levels After Leucine- or Methionine-Enkephalin Injection (5mg/kg.) | | | |
|---|---|---|---|---|
| | Compound | Route | N[1] | Prolactin[2] (ng/ml) |
| 1 | Control | SC | 10 | 29 ± 3 |
| | Met-Enkephalin | | 10 | 43 ± 3* |
| | Leu-Enkephalin | | 10 | 40 ± 6 |
| 2 | Control | SC | 9 | 40 ± 3 |
| | Met-Enkephalin | | 10 | 49 ± 3+ |
| | Leu-Enkephalin | | 10 | 40 ± 3 |
| 3 | Control | IV | 9 | 20 ± 1 |
| | Met-Enkephalin | | 9 | 24 ± 1+ |
| 4 | Control | IV | 7 | 43 ± 7 |
| | Leu-Enkephalin | | 8 | 29 ± 5 |
| 5 | Control | IV | 8 | 31 ± 3 |
| | Leu-Enkephalin | | 7 | 55 ± 5* |
| 6 | Control | IV | 8 | 47 ± 5 |
| | Leu-Enkephalin | | 7 | 59 ± 11 |
| 8 | Control | IV | 8 | 63 ± 10 |
| | Leu-Enkephalin | | 8 | 61 ± 10 |

[1] Number of animals per group
[2] Mean ± SEM; +p<0.05, *p<0.01 by analysis of variance Methionine-enkephalin administration (5 mg/kg.) resulted in a consistent, statistically significant increase in serum prolactin levels. The magnitude of the effect varied from 22 percent to 48 percent. A significant rise in prolactin levels was seen by either subcutaneous or intravenous routes. The change in prolactin levels upon the injection of leucine-enkephalin (also 5 mg/kg.) was more variable. Although some experiments indicated a significant increase in the prolactin levels, other experiments indicated no change in hormone levels.

EXAMPLE II

The effect of the enkephalins on prolactin release was also shown in rat pituitary cell culture.

Monolayer cultures of enzymatically dispersed pituitary cells were prepared from male rats, using Eagle's minimal essential medium for growth. After incubation in triplicate dishes for 3 hours at 37° C. in 95% air: 5% $CO_2$, the supernatant from each dish was assayed for prolactin in duplicate.

The results of the in vitro testing are shown in Table II.

TABLE II

| Prolactin Release in Monolayer Cultures of Rat Pituitary Cells | | |
|---|---|---|
| Concentration of Enkephalin | Prolactin Release[1] (ng/ml) | |
| | Met-Enkephalin | Leu-Enkephalin |
| 50 μg/ml | 307 ± 8* | 260 ± 15* |
| 5 | 255 ± 10* | 244 ± 10+ |
| 500 ng/ml | 305 ± 14+ | 253 ± 18+ |
| 50 | 257 ± 14+ | 254 ± 14+ |
| 5 | 261 ± 15+ | 247 ± 7+ |

TABLE II-continued

| Concentration of Enkephalin | Prolactin Release in Monolayer Cultures of Rat Pituitary Cells | |
|---|---|---|
| | Prolactin Release[1] (ng/ml) | |
| | Met-Enkephalin | Leu-Enkephalin |
| Control | 197 ± 13 | 197 ± 13 |

[1]Mean ± SEM; +p<0.05, *p<0.01 by analysis of variance (all values compared to control.)

Prolactin release was significantly increased by both methionine- and leucine-enkephalin at all levels from 5 ng/ml to 50 μg/ml. Methionine-enkephalin caused a greater release of prolactin than leucine-enkephalin, and at two levels this difference was statistically significant (50 μg/ml and 500 ng/ml).

What is claimed is:

1. A method for stimulating prolactin release in a warm-blooded animal in which such stimulation is desirable which comprises administering to said animal by a parenteral route an effective amount of a pentapeptide of the formula:

H-Tyr-Gly-Gly-Phe-Met-OH or

H-Tyr-Gly-Gly-Phe-Leu-OH or a non-toxic pharmacologically acceptable salt thereof.

2. A method as defined according to claim 1 wherein the formula of the pentapeptide is H-Tyr-Gly-Gly-Phe-Met-OH.

3. A method as defined according to claim 1 wherein the formula of the pentapeptide is H-Tyr-Gly-Gly-Phe-Leu-OH.

* * * * *